United States Patent [19]

Zamora et al.

[11] Patent Number: 5,700,444

[45] Date of Patent: *Dec. 23, 1997

[54] CHEMOTACTIC PEPTIDE PHARMACEUTICAL APPLICATIONS

[75] Inventors: Paul O. Zamora, Albuquerque, N. Mex.; Richard J. Freer, Richmond, Va.

[73] Assignee: Rhomed Incorporated, Albuquerque, N. Mex.

[*] Notice: The term of this patent shall not extend beyond the expiration date of Pat. No. 5,443,816.

[21] Appl. No.: 87,219

[22] Filed: Jul. 2, 1993

Related U.S. Application Data

[63] Continuation-in-part of Ser. No. 840,077, Feb. 20, 1992, Pat. No. 5,443,816.

[51] Int. Cl.$^6$ .......................... A61K 51/00; A61M 36/14
[52] U.S. Cl. ..................... 424/1.69; 424/1.11; 424/1.65
[58] Field of Search .................. 424/1.69, 9.1, 424/1.11, 1.65; 530/300, 324–330; 534/7, 10–16

[56] References Cited

U.S. PATENT DOCUMENTS

| | | | |
|---|---|---|---|
| 4,424,200 | 1/1984 | Crockford et al. | 424/1.1 |
| 4,427,646 | 1/1984 | Olexa et al. | 424/1.1 |
| 4,732,864 | 3/1988 | Tolman | 436/547 |
| 4,877,868 | 10/1989 | Reno et al. | 530/390 |
| 4,904,642 | 2/1990 | Coy et al. | 514/11 |
| 4,986,979 | 1/1991 | Morgan, Jr. et al. | 424/1.1 |
| 5,061,641 | 10/1991 | Shochat et al. | 436/545 |
| 5,091,514 | 2/1992 | Fritzberg et al. | 534/14 |
| 5,102,990 | 4/1992 | Rhodes | 530/391.5 |
| 5,128,119 | 7/1992 | Griffiths | 424/1.1 |
| 5,162,505 | 11/1992 | Dean et al. | 530/391.5 |
| 5,169,933 | 12/1992 | Anderson et al. | 530/391.3 |
| 5,225,180 | 7/1993 | Dean et al. | 424/1.1 |
| 5,371,184 | 12/1994 | Rajagopalan et al. | 530/324 |
| 5,443,816 | 8/1995 | Zamora et al. | 424/1.69 |

FOREIGN PATENT DOCUMENTS

| | | | |
|---|---|---|---|
| 2106235 | 9/1990 | Canada | 349/186 |
| 0196669 | 4/1986 | European Pat. Off. | C07K 17/06 |
| 0250013 | 5/1987 | European Pat. Off. | C07F 13/00 |
| 2225579 | 6/1990 | United Kingdom . | |
| WO 90/13317 | 11/1990 | WIPO . | |
| WO91/01144 | 2/1991 | WIPO . | |
| WO92/13572 | 2/1992 | WIPO | A61K 49/02 |
| WO92/13572 | 8/1992 | WIPO | A61K 49/02 |
| WO93/17719 | 9/1993 | WIPO | A61K 49/02 |
| WO93/25244 | 12/1993 | WIPO | A61K 49/02 |

OTHER PUBLICATIONS

Fischman, A.J., et al., "Imaging Focal Sites of Bacterial Infection in Rats with Indium–111–Labeled Chemotactic Peptide Analogs," *J. Nuclear Medicine*, vol. 32, No. 3, pp. 483–491 (1991).

Fischman, A.J., et al., Abstract, "Imaging of Focal Sites of Inflammation in Non–Human Primates with a TC99m–Labeled Chemotactic Peptide," *Proc. of 40th Ann. Meeting, Journal of Nuclear Medicine*, Abstract No. 415 (1992).

Vallabhaiosula, S., et al., "Evaluation of Technetium–99m Labeled Peptides for Imaging Infection in a Rabbit Model," *Proc of 40th Ann. Meeting, Journal of Nuclear Medicine*, vol. 34, No. 5, Abstract No. 414 (1993).

Babich, J.W., et al., "Technetium–99m–Labeled Chemotactic Peptides for Infection Imaging: Comparison with Indium–111–labeled Leukocytes in Infected Rabbits," *Proc. 40th Ann. Meeting, Journal of Nuclear Medicine*, vol. 34, No. 5, Abstract 833 (1993).

Babich, J.W., et al., "Tc99m–Labeled Hydrazino Nicotinamide Derivatized Chemotactic Peptide Analogs for Imaging Foci Sites of Bacterial Infection in Rabbits," *Proc. 40th Ann. Meeting, Journal of Nuclear Medicine*, vol. 34, No. 5, Abstract 836 (1993).

Kraus, J, et al., "Cyclic Tetrameric Clusters of Chemotactic Peptides as Superactive Activators of Lysozyme, Release from Human Meutrophils," *BioChem. and BioPhy. Res. Comm.*, vol. 124, No. 3 pp. 939–944 (1994).

Ravel, P., "Polymeric Analogues of N–formyl Peptides are Potent Activators of Degranulation and Superoxide Production by Human Neutrophils," *Biochem. and Biophys. Res. Comm.*, vol. 171, No. 1, pp. 266–272 (1980).

Cox, et al., "Technetium Labelled Somatostatin a Potential Agent for in Vivo Tumour Localization," *7th Intn'l Sympos. on Radiopharmacology*, Abstract, p. 16 (1991).

Fischman, Alan J., "A Ticket to Ride: Peptide Radiopharmaceuticals," *J. Nucl. Med.*, vol. 34, No. 12 pp. 2253–2263, (Dec. 1993).

Knaw, B.A., et al., "Technetium–99m Labeling of Antibodies to Cardiac Myosin Fab and to Human Fibregen," *J. of Nucl. Med.*, Basic Sciences, vol. 23, No. 11, pp. 1011–1019 (1982).

Kondo, M., et al., "Studies of Dimeric fMLF with High Chemotactic Activities," *Peptides—Chemistry and Biology*, Proc. of 12th Amer. Peptide Symp., Cambridge MA (Jun. 16–21, 1991).

Pimm, M.V., et al., "In labelling of a branched polypeptide drug carrier with a poly(L–lysine) backbone," *Int'l J. Pharm.*, Vo. 79 (1992), pp. 77–80.

*Primary Examiner*—John Kight
*Assistant Examiner*—Dameron Jones
*Attorney, Agent, or Firm*—Darby & Darby

[57] ABSTRACT

High affinity chemotactic peptides containing a biological-function domain which includes at least two linked N-formyl-Met-Leu-Phe sequences and a medically useful metal ion-binding domain are labeled with medically useful metal ions for use in a variety of diseases and pathologic conditions, and particularly for diagnosis and treatment of infections, inflammations and other diseases and conditions.

13 Claims, No Drawings

CHEMOTACTIC PEPTIDE PHARMACEUTICAL APPLICATIONS

CROSS-REFERENCE TO RELATED APPLICATIONS

This application is a continuation-in-part application of U.S. patent application Ser. No. 07/840,077, filed Feb. 20, 1992, now U.S. Pat. No. 5,443,816, entitled *Peptide-Metal Ion Pharmaceutical Preparation and Method;* and is related to U.S. Pat. No. 5,102,990, entitled *Direct Radiolabeling of Antibodies and Other Proteins with Technetium or Rhenium;* U.S. Pat. No. 5,078,985, entitled *Radiolabeling Antibodies and Other Proteins with Technetium or Rhenium by Regulated Reduction;* U.S. patent application Ser. No. 07/815, 122, filed Dec. 27, 1991 now abandoned, entitled *Composition for Radiolabeling Antibodies and Other Proteins by Regulated Reduction;* U.S. patent application Ser. No. 07/816,476, filed Jan. 3, 1992, now U.S. Pat. No. 5,346,687, entitled *Direct Radiolabeling of Antibody Against Stage Specific Embryonic Antigen for Diagnostic Imaging;* U.S. patent application Ser. No. 07/816,477, filed Jan. 3, 1992, now U.S. Pat. No. 5,460,785, entitled *Direct Labeling of Antibodies and Other Proteins with Metal Ions;* U.S. patent application Ser. No. 07/840,076, filed Feb. 20, 1992, now U.S. Pat. No. 5,277,892, entitled *Leukostimulatory Agent for In Vivo Leukocyte Tagging;* U.S. patent application Ser. No. 07/864,470, filed Apr. 6, 1992, now U.S. Pat. No. 5,277,893 entitled *Direct Radiolabeling of Substrates Containing Monosulfides or Disulfide Bonds with Radionuclides;* U.S. patent application 07/998,820, filed Dec. 30, 1992 entitled *IKVAV Peptide Radiopharmaceutical Applications;* and U.S. patent application Ser. No. 07/998,910, filed Dec. 30, 1992, entitled *YIGSR Peptide Radiopharmaceutical Applications;* the teachings of all of the foregoing are incorporated herein by reference.

LICENSE RIGHTS

The U.S. Government has a paid-up license in this invention and the right in limited circumstances to require the patent owner to license others on reasonable terms as provided for by the terms of Small Business Innovative Research Grant No. AI33276 awarded by the Public Health Service, Department of Health and Human Services.

BACKGROUND OF THE INVENTION

1. Field of the Invention (Technical Field)

This invention relates to chemotactic peptide-based metal ion-labeled compositions for use as pharmaceuticals, and methods of labeling with radiometals, paramagnetic metals and other medically useful metal ions, and further providing for use of medically useful metal ion-labeled chemotactic peptides for detection of infection, inflammation and other diseases and conditions.

2. Description of the Related Art, Including Information Disclosed under 37 C.F.R. Sections 1.97-1.99 (Background Art)

The use of biologically active peptides, which are peptides which bind to specific cell surface receptors or which in other ways modify cellular function, have received some consideration as radiopharmaceuticals. Canadian Patent Application 2,016,235, *Labeled Chemotactic Peptides to Image Focal Sites of Infection or Inflammation,* teaches a method of detecting a site of infection or inflammation, and a method for treating such infection or inflammation, by administration of a labeled or therapeutically-conjugated chemotactic peptide. In this application, the chemotactic peptides are chemically conjugated to DTPA and subsequently labeled with $^{111}$In. The utility of DTPA chelates covalently coupled to polypeptides and similar substances is well known in the art. Hnatowich, D J, U.S. Pat. Nos. 4,479,930 and 4,668,503. Other bifunctional chelates for radiolabeling peptides, polypeptides and proteins are well known in the art. Other biologically active peptides described include that disclosed by Olexa S A, Knight L C and Budzynski A Z, U.S. Pat. No. 4,427,646, *Use of Radiolabeled Peptide Derived From Crosslinked Fibrin to Locate Thrombi In Vivo,* in which iodination is discussed as a means of radiolabeling. In Morgan C A Jr and Anderson D C, U.S. Pat. No. 4,986,979, *Imaging Tissue Sites of Inflammation,* use of chelates and direct iodination is disclosed. In Tolman G L, U.S. Pat. No. 4,732,864, *Trace-Labeled Conjugates of Metallothionein and Target-Seeking Biologically Active Molecules,* the use of metallothionein or metallothionein fragments conjugated to a biologically active molecule, including peptides, is disclosed. The previous methods all employ some conjugation means with a bifunctional chelator in order to effectuate labeling with a radionuclide or other medically useful metal ion, such as a paramagnetic contrast agent. The only exception involves radioiodination; the iodine labeling of proteins or peptides containing tyrosine or histidine residues is well known, for example, by the chloramine-T, iodine monochloride, Iodogen or lactoperoxidase methods.

Chemotactic peptides are known to bind to neutrophils through discrete receptors and to result in regulation/ activation of various neutrophil receptors and stimulation of integrin-mediated adhesion. Specific types of neutrophil cell surface molecules which are upregulated by chemotactic peptides include CD14, CD15, CR3, and CD18. This, in turn, results in attachment of the neutrophils to activated endothelium and subsequent diapedesis to sites of infection. Blood-borne chemotactic peptides, therefore, stimulate circulating neutrophils to localize to sites of infection (e.g. sites of activated endothelium).

There is at present no simple, direct-labeled, radiopharmaceutical in general clinical use for the specific imaging of infections and inflammations. $^{67}$Ga-citrate and $^{111}$In-oxine-labeled white blood cells are currently used clinically, but both present significant limitations. $^{67}$Ga-citrate is not specific in its uptake into infections, and the radionuclide is not monoenergetic, has a relatively long half-life, and requires delayed imaging due to slow blood clearance. Use of $^{111}$In-oxine-labeled white blood cells has a much higher abscess specificity, however the labeling method is technically demanding and requires isolation of the patient's cells. Other methods, including the use of $^{99m}$Tc-human gamma globulin (non-specific), and $^{99m}$Tc-anti-granulocyte antibodies, have not come into routine clinical use. Potential drawback of radiolabeled antibodies include high manufacturing costs and the potential formation of human anti-mouse antibodies.

SUMMARY OF THE INVENTION

(DISCLOSURE OF THE INVENTION)

In accordance with the present invention, a high affinity chemotactic peptide-based pharmaceutical composition suitable for administration to a patient is provided. This composition, which may be lyophilized, includes at least two linked N-formyl-Met-Leu-Phe sequences, and a domain or region for binding medically useful metal ions. The portion of the composition made up of the two linked N-formyl-Met-Leu-Phe sequences forms at least a part of the biological-function domain of the composition. In one embodiment, the biological-function domain is a peptide sequence and linking agent including the following sequence:

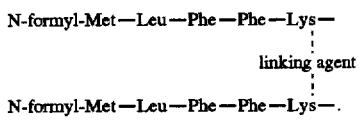

This peptide-based pharmaceutical composition can be selected from the group consisting of

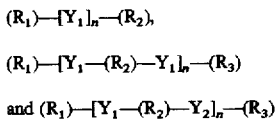

in which the medically useful metal ion-binding domain is selected from one of the group consisting of $[Y_1]_n$, $[Y_1-(R_2)-Y_1]_n$ and $[Y_1-(R_2)-Y_2]_n$ where n is a number between 1 and about 6 and $Y_1$ and $Y_2$ are amino acids comprising a sulfur, nitrogen or oxygen which is available for binding to metal ions or can be made available for binding to metal ions; the biological-function domain comprises at least one of the group consisting of $R_1$, $R_2$ and $R_3$; and those portions of $R_1$, $R_2$ and $R_3$ not comprising the biological-function domain each comprise an amino acid sequence containing from 0 to about 20 amino acids. In this structure, the medically useful metal ion-binding domain includes at least one amino acid sequence consisting of at least one amino acid selected from cysteine, cystine, histidine, penicillamine, deacylated methionine, lysine, arginine, aspartic acid, glutamic acid and tyrosine.

There are preferred peptide sequences for the medically useful metal ion-binding domain of the pharmaceutical composition, which sequences include:

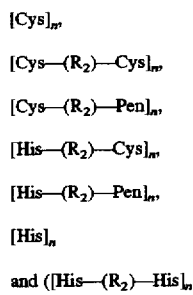

in which n is a number between 1 and about 6; and $R_2$ is an amino acid sequence containing from 1 to about 20 amino acids. It is also possible to employ other metal ion-binding domains, including chelates, and specifically bi-functional chelating agents.

The peptide-based pharmaceutical composition may also include a metal ion labeling agent. Stannous ion agents are a preferred metal ion labeling agent, with representative stannous ion agents including stannous tartrate, stannous glucoheptonate, stannous gluconate, stannous phosphonate, stannous chloride, and stannous fluoride.

The peptide-based pharmaceutical composition may also include the medically useful metal ion. The medically useful metal ion can include elements of iron, cobalt, nickel, copper, zinc, arsenic, selenium, technetium, ruthenium, palladium, silver, cadmium, indium, antimony, rhenium, osmium, iridium, platinum, gold, mercury, thallium, lead, bismuth, polonium and astatine. In many cases, the medically useful metal ion is a radionuclide, which may be an isotope of indium, gold, silver, mercury, technetium, rhenium or copper. Thus, it is possible for the medically useful metal ion to be radioactive.

This invention thus provides a method of performing a diagnostic procedure in a patient, in which the following steps are employed:

a) preparing a medically useful metal ion-labeled peptide comprising a peptide sequence comprising at least two linked N-formyl-Met-Leu-Phe sequences and a medically useful metal ion;

b) administering the medically useful metal ion-labeled peptide to the patient in a sufficient amount to accumulate at a target locus; and c) determining the locus of accumulation of the medically useful metal ion labeled peptide in the patient.

In this method, the diagnostic procedure to be employed to determine the locus of accumulation can most conveniently be metal ion detection imaging. For radioactive metal ions, various forms of gamma scintigraphy may be employed.

The diagnostic procedure can include detection of sites of neutrophil accumulation. In this way, several diseases or pathologies characterized by neutrophil accumulation may be diagnosed, including infections and sterile inflammations.

It is possible that the medically useful metal ion-labeled peptide employed in this method will include a chelating agent, whereby the medically useful metal ion is bound to the peptide via the chelating agent. It is also possible that the medically useful metal ion-labeled peptide will include a metal ion-binding domain, such that the medically useful metal ion-labeled peptide includes at least two linked N-formyl-Met-Leu-Phe sequences and a metal ion-binding domain, whereby the linked medically useful metal ion is bound to the peptide via the metal ion-binding domain.

This invention also generally provides for a high-affinity chemotactic peptide sequence suitable for use in targeting diagnostic or therapeutic agents to neutrophils in a patient, which peptide sequence includes at least two linked N-formyl-Met-Leu-Phe sequences. A variety of diagnostic or therapeutic agents may be employed, include radiometals, steroids, antibiotics, and immune system agents. These may be bound to or transported by the chemotactic peptide sequences by a variety of means, including chelates, bifunctional chelates, and any other chemical means.

Accordingly, it is an object of the present invention to provide for pharmaceutically useful chemotactic peptides comprising a biological-function domain incorporating two or more linked N-formyl-Met-Leu-Phe sequences and a medically useful metal ion-binding domain.

Another object of the invention is to provide a means to substantially increase the affinity of chemotactic peptides for their receptor by linking two or more N-formyl-Met-Leu-Phe sequences.

It is a further object of the present invention to provide a means whereby diseases and conditions involving accumulation of white blood cells, and more specifically accumulation of neutrophils, including infections and inflammations, can be diagnosed or treated.

It is a further object of the present invention to provide a means whereby metal ion-binding domains can be directly synthesized or genetically introduced into a chemotactic peptide incorporating two or more linked N-formyl-Met-Leu-Phe sequences, thereby allowing labeling without the necessity of conjugation to bifunctional chelators.

Another object of the present invention to provide a method for performing a diagnostic procedure by administration of a metal ion-labeled peptide composed of a biological-function domain incorporating two or more linked N-formyl-Met-Leu-Phe sequences and a metal ion-binding domain.

Another object of the present invention is to provide a method for the direct labeling of chemotactic peptides incorporating two or more linked N-formyl-Met-Leu-Phe sequences and amino acid sequences containing amino acids with sulfur, nitrogen or oxygen which is available or can be made available for binding metal ions, such as cysteine, histidine or penicillamine, or some combination thereof.

It is a further object of the present invention to provide a method to label chemotactic peptides incorporating two or more linked N-formyl-Met-Leu-Phe sequences with medically useful metal ions while retaining high biological activity subsequent to the labeling process.

Another object of the present invention is to provide a method and product which permit labeling to be accomplished by the end user using a single vial, containing a peptide with a biological-function domain incorporating two or more linked N-formyl-Met-Leu-Phe sequences and a medically useful metal ion binding domain and a metal ion labeling agent, which method requires only a single step to accomplish labeling, being the introduction of the medically useful metal ion.

Other objects, advantages and novel features, and further scope of applicability of the present invention will be set forth in part in the detailed description to follow and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF THE
PREFERRED EMBODIMENTS OF THE
INVENTION (BEST MODES FOR CARRYING OUT THE
INVENTION)

Using the methods of this invention, peptides with a biological-function domain comprising at least two or more linked N-formyl-Met-Leu-Phe sequences and a linked radiolabel provide materials useful for in vivo diagnostic applications, particularly for diagnostic imaging of infection, inflammation and other conditions characterized by accumulation of neutrophils. Preferably, the peptide comprises a biological-function domain comprising at least two or more linked N-formyl-Met-Leu-Phe sequences and a metal-ion binding domain comprising metal ion binding sequences which can be coupled directly with metal ions. The peptides can be prepared in a format providing a labeling kit which can, in turn, be used to prepare a metal ion-peptide complex for in vivo use. It is also possible to provide for labeling of a peptide with the biological-function domain with a metal ion in vivo, such as through use of a peptide-avidin complex, which is injected in vivo, followed by a biotin-metal ion complex inject in vivo, resulting in formation of an in vivo peptide-avidin-biotin-metal ion complex. The peptides of this invention preferably contain:

a) biological-function domains comprising at least two or more linked N-formyl-Met-Leu-Phe sequences, and b) metal ion-binding domains which can complex with medically useful metal ions.

The terms "bind," "binding," "complex," and "complexing," as used throughout the specification and claims, are intended to cover all types of physical and chemical binding, reactions, complexing, attraction, chelating and the like.

The biological-function domain of the preferred peptide is defined in the specification and claims as two or more linked peptide sequences which bind specifically to the chemotactic receptors found on the cell surfaces of white blood cells and, in particular, neutrophils. The preferred peptide sequence is two or more linked N-formyl-Met-Leu-Phe sequences, although other amino acids and amino acid sequences may be employed so long as they retain similar cellular and molecular specificity. The peptide of this invention thus preferably includes the sequence N-formyl-Met-Leu-Phe, which may be repeated two or more times, a linking agent, and optionally amino acids in addition to N-formyl-Met-Leu-Phe. Usually, within the indicated sequences, there may be modifications, including deletions, insertions, substitutions, cyclations or use of amino acid mimics. For the most part, substitutions will be conservative, in which amino acids having substantially the same conformation and polarity may be employed. The peptides may use L-amino acids, or one or more of the amino acids may be substituted by D-amino acids (D-stereoisomer). Particularly, one or more alanines may be substituted. In the alternative, terminal amino acids may be employed having unnatural chirality. The peptide may also include a terminal amide or a terminal acylated amino acid, particularly acetylated or alkylated, particularly methylated, amino acids. Where a cysteine provides the metal-ion binding domain at the N-terminus, the cysteine may be alkylated or unsubstituted on the mercaptan group.

The metal ion-binding domain of the peptide is defined in the specification and claims as a sequence of one or more amino acids containing sulfur, nitrogen or oxygen which is available for binding or can be made available for binding to metal ions. Sulfur-containing amino acids include primarily cysteine (Cys), cystine (Cys-Cys) and penicillamine (Pen), although deacylated methionine (Met), and other amino acids, may also be used. Useful nitrogen-containing amino acids include primarily histidine (His), but under certain conditions lysine (Lys) and arginine (Arg), which have $pK_a$ values of 10.0 and 12.0, and other amino acids, may also be employed. In addition, the terminal amino group of peptides may also be employed. Useful oxygen-containing amino acids include aspartic acid (Asp), glutamic acid (Glu), tyrosine (Tyr), serine (Ser) and threonine (Thr), as well as the terminal carboxyl group of peptides and other moieties. The amino acid sequences most usefully employed will include one or more Cys, one or more His, or a combination of Cys and His. Pen, which is an analogue of Cys, may be directly substituted for any given Cys. Cys may be present in the peptide as a disulfide in the form of cystine. The metal ion-binding domain may employ L-amino acids, or one or more of the amino acids may be substituted by D-amino acids (D-stereoisomer). The metal ion-binding domains may occur once or multiple times in any given peptide, and may occur in any combination. The metal ion-binding domain and the biological-function domain may overlap.

The metal binding sequences as found in the peptides of this invention may be stabilized by the addition of a positively-charged transition metal ion, such as Zn, Cu, Sn, Co, or Ni, and the like, selected to have a low order of binding strength. Through a replacement reaction, the transition metal ion replaces the H ion of the thiolate, imidazole or carboxyl group. The divalent ions of zinc and tin are thought to be particularly attractive. Some transition metals can simultaneously be used to reduce disulfide bridges and stabilize the metal binding sequences, such as Sn (II), which is particularly useful with cystine formations. In any case, the transition metals are weakly associated with the peptide.

The positively-charged transition metal ions are introduced to the peptide in an aqueous solution containing an appropriate buffer. The buffer may consist of dicarboxylic acids (tartrate, phthalate, citrate), amino acids (glycine, di-glycine, tri-glycine), borate, glucoheptonate, or the like. The buffer components may also be used as stabilizers for metal ions and/or as transfer agents or ligands for radionuclides, such as $^{99m}$Tc. For radiolabeling in acidic conditions, typically 10 mM tartrate and 40 mM phthalate at pH values of about 5 to about 7 are used. For radiolabeling in basic conditions, typically 10 mM glycine at pH values of about 8 to about 10 are used. The buffer may also contain a number of excipients and/or stabilizers including NaCl, inositol, glucoheptonate, and the like.

The peptide of this invention is complexed with a medically useful metal ion. The medically useful metal ion may be radioactive and generate gamma rays, beta particles, or positrons which are converted into gamma rays upon collision with electrons. Alternatively, the medically useful metal ion may be paramagnetic or supermagnetic. The medically useful metal ion may used in diagnostic imaging procedures including gamma scintigraphy, specific photon emission computerized tomography, positron emission tomography or magnetic resonance imaging.

Particularly useful metal ions can be found in the group consisting of elements 26–30 (Fe, Co, Ni, Cu, Zn), 33–34 (As, Se), 42–50 (Mo, Tc, Ru, Rh, Pd, Ag, Cd, In, Sn) and 75–85 (Re, Os, Ir, Pt, Au, Hg, Tl, Pb, Bi, Po, At). Isotopes of the elements Tc, Re, and Cu are particularly applicable for use in diagnostic imaging and radiotherapy. The isotope $^{99m}$Tc is particularly applicable for use in diagnostic imaging. Other radionuclides with diagnostic or therapeutic applications include $^{62}$Cu, $^{64}$Cu, $^{67}$Cu, $^{97}$Ru, $^{105}$Rh, $^{109}$Pd, $^{186}$Re, $^{188}$Re, $^{198}$Au, $^{199}$Au, $^{203}$Pb, $^{211}$Pb and $^{212}$Bi. The type of medically useful metal ion depends on the specific medical application. The medically-useful metal ion is selected to have a higher order of binding than the positively charged-transition metal ion used to stabilize the metal binding sequences. Radioisotopes of Tc are of significant interest, and particularly $^{99m}$Tc. In the case of $^{99m}$Tc, the peptides are reacted with sodium pertechnetate which has been treated with a reducing agent to generate Tc with a lower oxidation state. The product of the reaction between the metal ion and the peptide is a complex of the metal ion and the peptide. For example, the following structures could result from use of the invention, using Tc labeling of peptides containing metal-ion binding domains consisting of Cys and His groups as an example:

a) (biological-function domain)-[Cys]$_n$

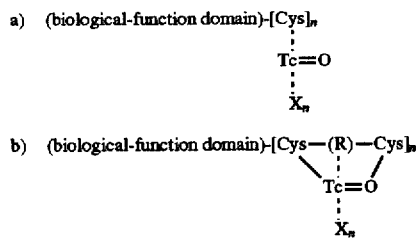

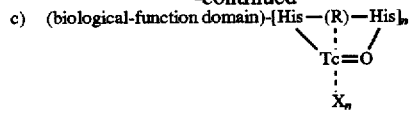

wherein R is an amino acid sequence containing from 1 to about 20 amino acids and $X_n$ is an anion, such as a halogen (e.g. fluoride or chloride), or a solvent molecule, such as water. In the foregoing, the biological-function domain is a peptide sequence including at least two or more linked N-formyl-Met-Leu-Phe sequences.

The resulting Tc-peptide bond should have a sufficiently high bond strength to minimize the exchange of the radionuclide to transferrin and serum albumin. The complex should be thermodynamically stable under varying physiological conditions and exhibit acceptable toxicological properties.

Most stannous reductions are performed at a pH of from about 5 to about 7. With amino acid side chains in a solution below pH 7, the basic amino acids are positively charged, the acidic amino acids are largely negatively charged, the alcoholic amino acids are neutral, and methionine is neutral. Since reduced technetium binds more readily to neutral hydrogen donors rather than positively charged hydrogen donors, at the pH range 5 to 7 only Cys and His are optimal $^{99m}$Tc binding site candidates. For both Cys and His, radiolabeling yields are dependant on pH, and are theoretically optimal at or near the $pK_a$.

It is also possible to administer the peptide comprising two or more linked N-formyl-Met-Leu-Phe sequences, and to perform the actual radiolabeling in vivo. This can be done, for example, using a biotin-avidin system, in which biotin is conjugated to the peptide, which is then injected into the patient. A radioisotope-labeled avidin complex is then injected, which binds to the peptide-biotin complex, forming a peptide-biotin-avidin-radiolabel complex, which can be detected by gamma scintigraphy or other detection means. This method presents certain advantages, in that maximum clearance and target binding parameters can be attained. To use this system, for example, it is possible to employ Biotin-HPDP (Pierce Chemical Co.), a clearable, sulfhydryl-reactive biotinylation reagent. The peptide is dissolved in a 100 mM borate buffer pH 8.0 to a final concentration of 1 mg/ml, and biotin-HPDP at 1 mg/ml is added. The solution is mixed and incubated for 1 hour, and the biotinylated peptide separated from unconjugated materials by molecular sieve chromatography over Sephadex G-25. Avidin or strepavidin can be directly iodinated with $^{131}$I by standard methods. Alternatively, avidins can be conjugated to chelating agents such as DTPA or other agents which introduce thiols into the protein, and radiolabeled with $^{99m}$Tc. For use in vivo, the biotinylated peptide is injected intravenously and allowed to localize and clear from the general circulation, a time period generally of from 1 to 2 hours. Radiolabeled avidin is then injected; the radiolabeled avidin binds to the biotin, and consequently localizes the disease lesion.

The peptides of the invention can be:

a) naturally-occurring, b) produced by chemical synthesis, c) produced by recombinant DNA technology, d) produced by biochemical or enzymatic fragmentation of larger molecules, e) produced by methods resulting from a combination of a-d, or f) produced by any other means for producing peptides.

By employing chemical synthesis, the preferred means of production, it is possible to introduce various amino acids which do not naturally occur along the chain, modify the N- or C-terminus, and the like, thereby providing for greater lifetime of the peptide, improved stability and formulation, resistance to protease degradation, and the like. The term "peptide" as used throughout the specification and claims is intended to include any structure comprised of two or more amino acids. For the most part, the peptides of this invention comprise fewer than 60 amino acids, and preferably fewer than 30 amino acids, and most preferably ranging from about 10 to 30 amino acids.

The product resulting from the methods set forth herein can be used for both medical applications and veterinary applications. Typically, the product is used in humans, but may also be used in other mammals. The term "patient" is intended to denote a mammalian individual, and is so used throughout the specification and in the claims. The primary applications of the invention involve human patients, but the invention may be applied to laboratory, farm, zoo, wildlife, pet or sport animals.

The product may be used to monitor normal or abnormal metabolic events, to localize normal or abnormal tissues, to localize diseases, and to bind to blood constituents, including blood cells, and most preferably neutrophils, for subsequent localization of diseases, infections, and abnormal tissues. There is a wide variety of clinical conditions characterized by severe inflammation. Hidden, or occult, abscesses are particularly difficult to diagnose accurately. These lesions can be caused by a variety of bacteria and may be localized in any organ system. The location can be crucial to the choice of antibiotic or other therapy. Other significant conditions involving inflammatory loci include inflammatory bowel disease, appendicitis, opportunistic infections in patients with AIDS, and the inflammation associated with organ transplants and surgically implanted prostheses. Acute inflammatory disease may be life threatening; some types of abscesses have an overall mortality of 40%. Prompt diagnosis and treatment is crucial to patient survival.

The product can be used in a variety of medical procedures including gamma scintigraphy, specific photon emission computerized tomography, positron emission tomography, and magnetic resonance imaging. It is also possible to use the product to deliver a therapeutic quantity of radiation to a disease site. The medical application of the product of this invention depends on the type of peptide and the type of medically useful metal ion used.

In Zamora P O and Rhodes B A, U.S. patent application Ser. No. 07/840,077, entitled Peptide-Metal Ion Pharmaceutical Preparation and Method, which application is incorporated herein by reference, the use of peptide-based metal-ion labeled compositions as pharmaceuticals is taught, together with methods of labeling peptides, proteins and other similar substances with radiometals, paramagnetic metals and other medically useful metal ions. This invention also teaches that peptides containing a biological-function domain and a medically useful metal ion-binding domain can be labeled with medically useful metal ions for use in diagnosis and treatment of a variety of pathologic conditions. Accordingly, the teachings of this application are incorporated herein by reference.

The metal ion-binding domain of the peptide involves one or more amino acids containing sulfur, nitrogen or oxygen which is available for binding, or which can be made available for binding to metal ions. Commonly used amino acids include Cys, Pen and His, or any combination thereof. The simplest case takes the form $(R_1)$—$[Cys]_n$—$(R_2)$ wherein $[Cys]_n$ is the medically useful metal ion-binding domain and n is typically a number between 1 and about 6; and $R_1$ and $R_2$ are each an amino acid sequence containing from 0 to about 20 amino acids, with at least $R_1$ and $R_2$ including the biological-function domain. In this and all related forms, it should be noted that $R_1$ and $R_2$ are interchangeable; either can contain the biological-function domain, the biological-function domain may include part or all of both $R_1$ and $R_2$, and the biological-function domain may constitute only a portion of the amino acid sequence in either $R_1$ or $R_2$. The order of components for these purposes can be varied, so that $(R_1)$—$[Cys]_n$—$(R_2)$, $(R_2)$—$[Cys]_n$—$(R_1)$, $[Cys]_n$—$(R_2)$—$(R_1)$, $[Cys]_n$—$(R_1)$—$(R_2)$ and the mirror images of the last two orderings are all equivalent, even though the resulting peptides may significantly differ in other aspects.

Other forms of the same general configuration include $(R_1)$—$[Cys$—$(R_2)$—$Cys]_n$—$(R_3)$, $(R_1)$—$[Cys$—$(R_2)$—$Pen]_n$—$(R_3)$, $(R_1)$—$[His$—$(R_2)$—$Cys]_n$—$(R_3)$, $(R_1)$—$[His$—$(R_2)$—$Pen]_n$—$(R_3)$, and $(R_1)$—$[His$—$(R_2)$—$His]_n$—$(R_3)$ wherein the sequence $[. . .]_n$ is the medically useful metal ion-binding domain with n typically being a number between 1 and about 6; and $R_1$, $R_2$ and $R_3$ are each an amino acid sequence containing from 0 to about 20 amino acids, with at least one of $R_1$, $R_2$ and $R_3$ including the biological-function domain. Here too the ordering is irrelevant to the functional description; for example, $(R_3)$—$[His$—$(R_2)$—$Cys]_n$—$(R_1)$, $(R_1)$—$(R_3)$—$[His$—$(R_2)$—$Cys]_n$, $(R_3)$—$(R_1)$—$[His$—$(R_2)$—$Cys]_n$, mirror images of the foregoing two orderings, all orderings in which the positions of His and Cys are reversed, and orderings in which the biological-function domain is present in any of the three regions $R_1$, $R_2$ and $R_3$, any portion of the three regions $R_1$, $R_2$ and $R_3$, or any combination of the three regions $R_1$, $R_2$ and $R_3$, are all equivalent to the third configuration listed above, $(R_1)$—$[His$—$(R_2)$—$Cys]_n$—$(R_3)$. Each of the other foregoing configurations can be similarly described.

In one preferred embodiment of the method for labeling peptides of the configurations set forth above, the following method can be employed:

a) adding a source of positively-charged transition metal, most preferably a Sn (II) agent, to the peptide containing amino acids comprising sulfur, nitrogen or oxygen which is available for binding, or which can be made available for binding to metal ions, in an amount sufficient to allow the positively-charged transition metal to undergo a replacement reaction, thereby forming transition metal-containing and sulfur-, nitrogen- or oxygen-containing complexes, or some combination thereof; and, b) adding a medically useful metal ion whereby the metal ion displaces the transition metal in the transition metal-containing and sulfur-, nitrogen- or oxygen-containing complexes and the metal ion and peptide form metal ion-containing and sulfur-, nitrogen-, or oxygen-containing complexes.

The preferred transition metal is Sn (II); useful sources of Sn (II) include stannous tartrate, stannous glucoheptonate, stannous gluconate, stannous phosphonate, stannous chloride, and stannous fluoride. The selection of the source of Sn (II) and its final concentration depends on the intended medical application of the peptide, the nature of the peptide, the relative and absolute number of thiolate groups and the metal ion to be used. In one embodiment stannous tartrate is used at a concentration of 1.25 mM. The stannous tartrate is prepared in a buffer composed of 10 mM tartrate and 40 mM phthalate, pH 5.6, and is added to peptide to yield a final concentration of 1 mg/ml peptide solution.

Sn (II) can be stabilized by use of carboxylic acids, such as acetate, citrate, phthalate and tartrate. A wide range of dicarboxylic acids, known to those skilled in the art, may be similarly used to stabilize the Sn (II) and/or to act as a buffer. If the phthalate and tartrate are in molar excess relative to the Sn (II), then these dicarboxylic acids also stabilize the medically useful metal ion in a form which can react with the peptide. In one embodiment, tartrate and phthalate are used in the Sn (II) agent at concentrations of 10 mM and 40 mM, respectively.

Similarly, the Sn (II) and the medically useful metal ion may be stabilized by free amino acids used singly or in combination with other agents. The type of amino acid used and the specific concentration depends on the nature of the peptide and its intended use. In one embodiment, glycine is used at a concentration of 0.1–10 mM, and in another, histidine is used at a concentration of 0.1–10 mM. In yet another embodiment, trace amounts of thiol-containing agent, such as cysteine, may be added to stabilize the Sn (II) and the medically useful metal ion.

The peptide may be stored in bulk form or in unit dose form after addition of the Sn (II) or other transition metal. For example, in one embodiment the peptide is stored at −20° C. in vials after introduction of the Sn (II). Methods used in lyophilization of peptides are known to those skilled in the art. Either frozen or lyophilized preparations may be maintained for an indefinite period before labeling by the addition of the medically useful metal ion.

In both the frozen and lyophilized storage forms, excipients may be added to the peptide to minimize damage which can arise from ice-crystal formation or free-radical formation. The type of excipient and the concentration depends on the nature of the peptide and the intended use. In one embodiment, glycine and inositol are used as excipients in lyophilized preparations.

A typical lyophilized preparation made by the embodiments set forth above would, upon rehydration, contain 10 mM tartrate, 40 mM phthalate, 22 µg of Sn (II), 500 µg of peptide, 2 mg/ml of glycine, and 2 mg/ml of inositol. To label with a medically useful metal ion, a typical lyophilized preparation is hydrated by the addition of a solution containing 0.9% NaCl (U.S.P.) or water for injection (U.S.P.) and the medically useful metal ion. Alternatively, it is possible to hydrate the lyophilized preparation, and to add the metal ion in a subsequent step. If a frozen preparation is used, it is thawed and allowed to come to room temperature, and a solution containing the medically useful metal ion is then added. The nature and amount of the medically useful metal ion and the specific reaction conditions depend on the isotopic nature of the metal, and the intended medical application. In one embodiment, $^{99m}$Tc is added in the form of pertechnetate ion in a solution of 0.9% NaCl. The $^{99m}$Tc is typically incubated for up to 30 minutes to insure completion of the reaction with the peptide, after which the radiolabeled preparation can be directly used in medical applications. In another embodiment, the $^{99m}$Tc is reduced and complex to a transfer agent such as glucoheptonate, tartrate or the like, and the reduced and complexed $^{99m}$Tc is then added to the peptide preparation and allowed to incubate, thereby allowing transfer of the $^{99m}$Tc to the peptide.

In the embodiment in which $^{99m}$Tc is used, the Sn (II) is present in the peptide-containing solution in sufficient excess to alter the oxidation state of the Tc ion such that it can bind to ionizable groups. Similar approaches may be used to lower the oxidation state of other medically useful metal ions for subsequent binding to ionizable groups. The type of the metal ion, its isotopic nature, and concentration would depend on the intended medical application.

It is also possible to construct a peptide wherein the biological-function domain contains two or more linked N-formyl-Met-Leu-Phe sequences and the peptide further contains a metal ion-binding domain including one or more disulfide bonds. In that case, it is necessary to first reduce the disulfide bond or bonds. In a preferred method, the following steps are employed:

a) incubating the peptide with a reducing agent to reduce some or all of the disulfide bonds to thiolate groups;

b) removing excess reducing agent from the peptide substrate containing thiolate groups;

c) adding a source of Sn (II) agent to the thiolate-containing peptide preparation in an amount sufficient to form Sn (II)-containing and sulfur-containing complexes; and, d) adding a medically useful metal ion whereby the metal ion displaces the Sn (II) in the Sn (II)-containing and sulfur-containing complexes and the metal ion and thiolate-containing peptide form metal ion-containing and sulfur-containing complexes.

The order of the steps may be altered, and the method will still produce metal ion-labeled peptides. Accordingly, the claims are not limited to the order of steps presented therein. Specifically, it is possible, and in some cases advantageous, to add the Sn (II) to form Sn (II)-containing and sulfur-containing complexes prior to removing excess reducing agent from the peptide substrate. In this way, oxidation of thiolate groups or reformation of disulfide bonds and other cross-linkages is immediately minimized.

Different configurations of peptides with one or more disulfide bonds are possible, and can be labeled as set forth herein. The most common example is the form

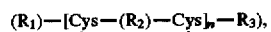

wherein $[Cys—(R_2)—Cys]_n$ is the medically useful metal ion-binding domain, which can appear in the amino acid sequence from 1 time to about 6 times; and $R_1$, $R_2$ and $R_3$ are each amino acid sequences containing from 0 to about 20 amino acids, with at least one of the amino acid sequences $R_1$, $R_2$ and $R_3$ comprising the biological-function domain. Other peptide configurations in which reducible disulfide bonds are present are also included in this method. These include the substitution of Pen for one or both Cys amino acids, as well as the modification of a native Met to allow it to form a disulfide bond. The biological-function domain can appear in any one of $R_1$, $R_2$ and $R_3$, and can also span more than one region, so that the biological-function domain may comprise, for example, $R_2$ and $R_3$, or some portion of $R_2$ and $R_3$. Any one or more of the regions $R_1$, $R_2$ and $R_3$ may contain no amino acids.

Numerous reducing agents have been described and are known to those skilled in the art. Particularly useful types of reducing agents include 2-mercaptoethanol; 1,4-dithiotheitol; 2,3-dihydroxybutane-1,4-dithiol;

2-aminoethanethiol HCl; 2-mercaptoethylamine; thioglycolate; cyanide; cysteine; reduced glutathione; Sn (II); Cu (I); and Ti (II). The reducing agent may be dissolved in a solute or may be attached to a solid phase. Reducing agents attached to a solid phase are commercially available, and methods for their use are known to those skilled in the art. The degree to which the peptide requires disulfide bond reduction depends on the nature of the peptide and its intended medical application. Generally speaking, milder reduction conditions and shorter incubation periods are normally employed than are required to reduce disulfide bonds in proteins or complex polypeptides, such as antibodies. In any event, reduction is halted before excessive fragmentation of the peptide or loss of the biological-function of the peptide occurs.

In one specific embodiment, Sn (II) is used as a reducing agent at a concentration of 5 mM. In this embodiment the Sn (II) is dissolved in a buffer composed of approximately 10 mM tartrate and 40 mM phthalate, pH 5.5, and the Sn (II) buffer admixed with a peptide substrate at a concentration of 8.3 mg/ml. The reduction reaction is allowed to proceed for a period of time at room temperature, three hours having been employed successfully with some peptides containing a single disulfide bond, after which time the reaction is terminated by removing excess Sn (II) ions by molecular sieve chromatography. One means of molecular sieve chromatography employs Sephadex G-25, with the chromatography gel pre-equilibrated, and the peptide eluted in 0.9% NaCl or other suitable buffer.

Removal of the reducing agent, whether Sn (II) or some other reducing agent, can be accomplished by a variety of suitable means, including such methods as dialysis, ultrafiltration, positive-pressure membrane filtration, precipitation, preparative high performance liquid chromatography, affinity chromatography, other forms of chromatography and preparative isoelectric focusing. Many of the reducing agents contain thiols, which if present in the final labeling mixture, can complex with the medically useful metal ion. Such complexes can have severe and unknown side effects if administered in vivo. Additionally, some reducing agents exhibit unacceptable toxicity. Thus removal of the reducing agent both limits the degree of reduction to that desired, as well as providing for increased utility and safety of the labeled preparation by removal of toxic or otherwise undesirable reducing agents.

Thiolate groups in reduced peptides are highly reactive and can interact to reform disulfide bonds. The use of Sn (II) is believed to minimize the reformation of disulfide bonds. Sources of Sn (II) include stannous tartrate, stannous glucoheptonate, stannous gluconate, stannous phosphonate, stannous chloride, and stannous fluoride. The selection of the source of Sn (II) and its final concentration depends on the intended medical application of the peptide, the nature of the peptide, the relative and absolute number of thiolate groups and the metal ion to be used. In one embodiment stannous tartrate is used at a concentration of 1.25 mM. The stannous tartrate is added to the peptide after removal of the peptide-reducing agent. The stannous tartrate is prepared in a buffer composed of 10 mM tartrate and 40 mM phthalate, pH 5.6, and is added to peptide to yield a final concentration of 1 mg/ml peptide solution.

The biological-function domain of the chemotactic peptide of this invention has substantially higher affinity than peptides containing a single N-formyl-Met-Leu-Phe sequence. The linked peptide sequence, synthesized as a symmetric dimer without a metal-ion binding domain, has a 50% effective concentration (EC$_{50}$) of $6.1 \times 10^{-12}$M in the rabbit neutrophil lysosomal-enzyme-release assay. This EC$_{50}$ is approximately 100 fold higher in activity than formylated peptides containing a single N-formyl-Met-Leu-Phe sequence. The linked peptide sequence is:

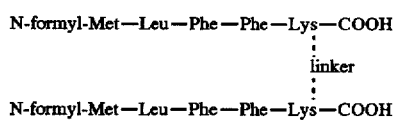

The linker portion is based on the use of a succinate as a bridge. The succinate can be introduced by use of succinic ONSu ester (solid phase) or by succinate-mediated fragment condensation with a water soluble diimide (solution phase), and results in the following structure, where NH is the epsilon amino group of Lys:

The metal ion-binding domain may be added to the carboxy-terminal end of the peptide. A variety of metal ion-binding domains may be employed; one preferred domain is the sequence Gly-His-Gly-Gly-Cys-OH, which then provides the following composition:

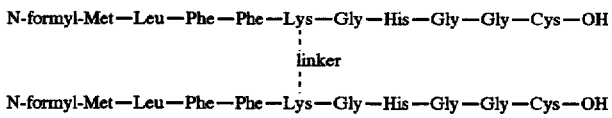

This composition is designed to retain an EC$_{50}$ at or near $6.1 \times 10^{-12}$ M and be able to bind a maximum of two $^{99m}$Tc molecules, thereby providing the highest specific activity possible. The peptide linkage through the lysine groups is designed to provide protease resistance at that site. To provide a higher degree of protease resistance, (D)-alanine can be introduced between Lys$^5$ and His$^6$ and the cysteine amidated to provide the compound:

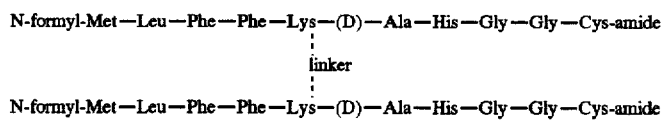

Both this composition and its parent are designed to have a relatively high hydrophobic moment, and as a consequence to be cleared at least in part to the liver. To increase kidney clearance one glycine at the carboxy terminal end may be substituted with a glutamic acid to provide the following construction:

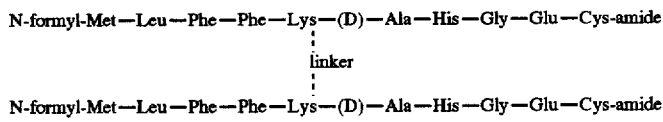

Peptides can be prepared, depending on the design, by either conventional solid-phase t-butyloxycarbonyl (t-Boc) or 9-fluoroenylmethoxyycaronyl (FMoc) protocols or classical solution phase (rapid mixed-anhydride) synthesis. Formylation can conveniently be accomplished by dicyclohexylcarbodiimide (DCC)/hydroylbenztriazole (HOBT) coupling of formic acid (solid phase) or by the method of Day et al. (1980) for solution phase. Deprotection can conveniently be accomplished by anhydrous trifluoroacetic acid (TFA) (FMoc protocol), anhydrous hydrofluoric acid (t-Boc protocol) or catalytic hydrogenation (benzyl esters prepared by solution phase). Purification is conventionally accomplished by reverse phase HPLC.

Thus, to construct a peptide of this invention, a synthesis scheme can be employed in which a t-Boc-Cys (p-MeOBzl) -resin is used with standard t-Boc chemistry to prepare the linear sequences. A tosyl (Tos) is used to protect the imidazole of histidine and FMoc used to protect the epsilon-amino group of Lys. The formyl group is added by coupling of formic acid using the same DCC/HOBT protocol as for the protected amino acids. Subsequently, the FMoc group is removed in 20% piperidine in N-methyl-pyrrolidone, and two identical peptide chains coupled with succinic-N-hydroxysuccimide ester. The reaction is monitored using ninhydrin and, when complete, the peptide resin is treated with anhydrous HF to generate the desired peptide. The crude product is purified by HPLC.

A variety of linkers may be employed, in addition to dicarboxylic acids such as succinic-N-hydroxysuccimide ester. For example, the linker can be composed of diethyl amine, having the structural formula $H_2N-CH_2-CH_2-NH_2$, or other diamine compounds. The diamine compounds may be conjugated to peptides using carboxylated side chains of the peptide, such as terminal carboxyls, Gly, Asp, or combinations. Such a linker might be employed to construct a symmetric dimer having the following composition:

There are a number of homo- and hetero-bifunctional crosslinking agents which have been described, and are known to those skilled in the art. These agents may also be employed in this invention.

Asymmetric dimers are also provided in which, for example, the Cys residues are moved relative to each other, or other specific sequences added to improve clearance. A solid-phase strategy may be employed using either t-Boc-Orn (FMoc) or t-Boc-Lys (FMoc) resins as the starting material. In this method, one chain is built through the alpha amino group using conventional t-Boc chemistries. Subsequently, the FMoc group is removed and a second chain, which may be identical or different, is constructed using conventional FMoc chemistries. Formyl groups are introduced as formic acid using DCC/HOBT and the Cys and His side chains are be protected with the MeOBzl and Tos groups, respectively. Cleavage and deprotection can be performed with anhydrous HF with purification by reverse phase HPLC.

Alternate peptide sequences include the following:

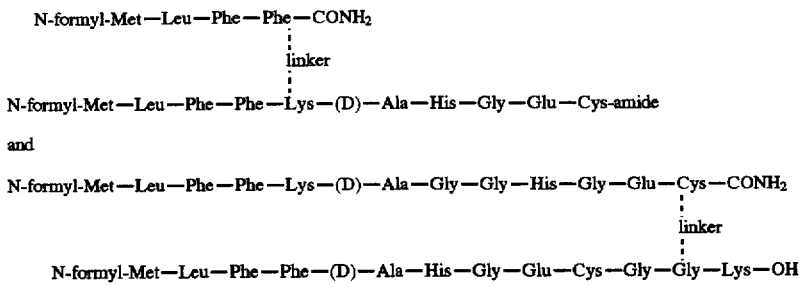

Use of D-amino acids is designed to confer resistance to protease degradation of the peptide. In these examples, use of only one $^{99m}$Tc-binding sequence is designed to minimize intramolecular crosslinking. The use of asymmetric $^{99m}$Tc-binding sequences also minimizes interchain crosslinking through the $^{99m}$Tc.

In one embodiment, radiolabeling kits are made using the peptide sequences shown above. All steps are performed using aseptic technique, with all solutions purged with nitrogen, filtered through a 0.22 micron pore-size filter, and stored under a head-space gas of nitrogen. Any of the peptides shown above are dissolved in 10 mM/40 mM tartrate/phthalate buffer, pH 5.6, containing 0.9% NaCl to a concentration of 2 mg/ml. After dissolution, the peptide solutions are mixed 1:1 (v/v) with buffer containing 5 mM stannous tartrate. The solution is then incubated for 24 hours at room temperature. After incubation period, the solution is filtered through an ion exchange column (QMA-type, Millipore, Corp.) to remove spurious tin colloid and excess complexed tin ions. The peptides eluting in the void volume is mixed 1:1 (v/v) with a buffer resulting in a final concentration of 10 mM tartrate/40 mM phthalate/0.6 mM stannous tartrate, at pH 5.6. The resulting peptide will then have the structure:

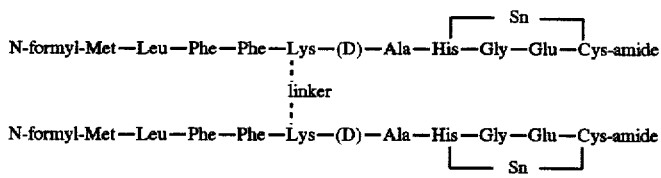

Excipients, including lyophilization stabilizers, can also be introduced in this step. Glycine, inositol and other excipients serve to stabilize the proteins for subsequent lyophilization. After lyophilization, the kits can be radiolabeled with $^{99m}$Tc.

The kits are designed for direct radiolabeling, using stannous ions to reduce $^{99m}$Tc. To radiolabel, the lyophilized kits are rehydrated with 0.9% NaCl (U.S.P.), and after dissolution varying amounts of $^{99m}$Tc (sodium pertechnetate) added. During the radiolabeling, low amounts of stannous ions, present in excess, are used to reduce pertechnetate (Tc-VII) to a lower oxidation state (Tc-V). The reduced technetium is believed to undergo a replacement reaction with the peptide-bound tin ions, resulting in the final $^{99m}$Tc-labeled complex illustrated below:

containing 2% maltose. The peptide solution was mixed (1:1) with P/T buffer containing 1.25 mM stannous tartrate. Aliquots (typically 0.25 ml containing 250 µg of peptide) were then sterile filtered through a 0.22 micron filter, and dispensed into individual vials. The head space of each vial was purged with nitrogen, the vials stoppered and crimped, and stored frozen at −70° C. For radiolabeling, the contents of a vial was allowed to come to room temperature and $^{99m}$Tc (sodium pertechnetate) added. After 30 minutes, the materials were used in experiments. In some cases, the buffer components were altered by the addition of glycylglycine so that the pH could be adjusted up to a high of pH 8.6.

To determine the relative amount of $^{99m}$Tc bound to a given peptide preparation, aliquots of the $^{99m}$Tc-labeled preparations were analyzed by molecular sieve HPLC, reverse phase chromatography, and thin layer chromatography.

The initial radiolabeling studies with histidine-containing peptides were conducted at a pH of 5.6, and binding was observed for all the peptides examined. The order of binding

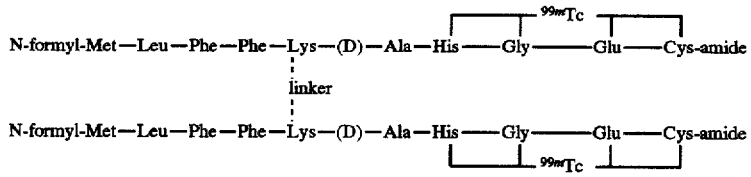

The excess tin ions site-protect any thiolates not directly involved in $^{99m}$Tc-binding.

The invention is further illustrated by the following non-limiting examples.

was essentially the same in all analytical systems used to assay binding, radiometric HPLC, TLC (for unbound pertechnetate), and reverse phase chromatography. The relative percentage $^{99m}$Tc associated with the peptide, in decreasing order, is shown in Table 1

TABLE 1

| PEPTIDE | % BINDING BY RADIO-HPLC |
| --- | --- |
| N-formyl-Met—Leu—Phe—Gly—Gly—His—Gly—Gly—Cys (SEQ. ID NO. 1) | 89% |
| N-formyl-Met—Leu—Phe—Gly—His—Gly—Gly—His—Gly—His—Gly—Gly—His (SEQ. ID NO. 2) | 82% |
| N-formyl-Met—Leu—Phe—Gly—Gly—His—Glu—Lys—Gly—His—Gly—His—Trp (SEQ. ID NO. 3) | 46% |
| N-formyl-Met—Leu—Phe—Gly—Gly—His—Trp (SEQ. ID NO. 4) | 42% |

EXAMPLE 1—EVALUATION OF METAL-ION BINDING DOMAINS

To evaluate the effectiveness of different metal-ion binding domain peptide sequences, different sequences were evaluated using a peptide containing a single N-formyl-Met-Leu-Phe sequence. Each peptide was dissolved to a final concentration of 2.0 mg/ml in chilled, nitrogen-purged 10 mM tartrate/40 mM phthalate buffer, pH 5.6 (P/T buffer)

TLC was used to measure the amount of peptide-bound (and unbound) $^{99m}$Tc and the amount of radiolabeled aggregate/colloid. Both measurements involved the use of TLC-SG (Gelman Sciences, #61886) chromatography paper, cut into 1.5×10 cm strips and activated by heating for 30 minutes at 110° C., as per the manufacturer's instructions. Only small amounts of radiocolloid (less than 1%) were found in all of the preparations as determined by TLC over albumin-coated TLC strips and using a MeOH/ammonia/water solvent.

Radiometric molecular-sieve HPLC was performed using a 7.5×300 mm TSK G3000SW column preceded with a TSK-SW 7.5×75 mm guard column (TosoHaas, Philadelphia, Pa.) at a flow rate of 1 ml/minute phosphate buffered saline (0.01 M phosphate, pH 7.0, containing 0.15 M NaCl), with a UV and radioisotope detector in series. Radiometric HPLC used in a molecular sieve mode revealed that all of the chemotactic peptides radiolabeled and eluted in a position which was distinct from that obtained with $^{99m}$Tc-pertechnetate. However, the position of elution did not necessarily correspond to the theoretical molecular weight of the peptides. This distortion in molecular weight profile is thought to be due to the fact that the peptides are near or below the practical resolving capacity of the HPLC column used (molecular sieve type).

EXAMPLE 2—EFFECT OF pH ON RADIOLABELING KITS

To evaluate the possibility that pH could contribute to an increase in labeling efficiency, the peptide:

N-formyl-Met-Leu-Phe-Gly-His-Gly-Gly-His-Gly-His-Gly-Gly-His (SEQ. ID NO.2) was formulated in radiolabeling kits at pH values of 5.6, 6.6, 7.6, and 8.6. In these preparations, the buffer was composed of 20 mM citrate and 50 mM glycylglycine containing 0.6 mM stannous tartrate. The use of glycylglycine was found to keep the stannous ions in solution without the formation of colloid. In these studies the most effective pH for radiolabeling was found to be 7.6 as demonstrated using HPLC and confirmed by TLC using saline as a developer. At pH 5.6 doublet peaks were observed by HPLC analysis. The lead peak decreased noticeably at pH 6.6, was absent at pH 7.6, and reappeared at pH 8.6. In TLC studies using saline as a developer, the amount of radiolabel at the origin increased up to pH 7.6 and then fell dramatically, as is shown in Table 2 presented below.

TABLE 2

Effect on radiolabeling of varying the pH of radiolabeling kits of the peptide sequence N-formyl-Met—Leu—Phe—Gly—His—Gly—Gly—His—Gly—His—Gly—Gly—His (SEQ. ID NO. 2)

| pH OF LABELING | TYPE OF HPLC PEAK | HPLC % RECOVERY | TLC % cpm AT ORIGIN | TLC % COLLOID |
|---|---|---|---|---|
| 5.6 | doublet | 61.5 | 88.7 | 3.0 |
| 6.6 | doublet | 84.6 | 96.0 | 2.9 |
| 7.6 | singlet | 100.5 | 98.0 | 5.5 |
| 8.6 | doublet | 11.9 | 10.0 | 12.5 |

EXAMPLE 3—PREPARATION OF PEPTIDE CONTAINING TWO LINKED CHEMOTACTIC SEQUENCES

A peptide of the following configuration is constructed using conventional means:

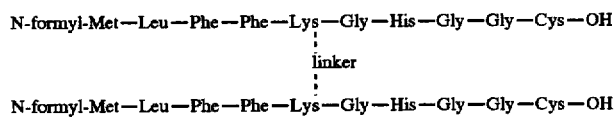

The peptide is solubilized in a buffer, allowed to incubate, and purified by ion exchange column chromatography, resulting in a peptide in a buffer composed of 10 mM tartrate, 40 mM phthalate, and 0.6 mM stannous tartrate, at pH 5.6. The peptide is radiolabeled by the addition of sodium pertechnetate $^{99m}$Tc.

EXAMPLE 4—USE OF PEPTIDE CONTAINING TWO LINKED CHEMOTACTIC SEQUENCES

A radiolabeled peptide containing two linked chemotactic sequences, such as the peptide of Example 3, is prepared. The preparation is injected into a patient suspected of having an internal infection or inflammation, and after a suitable period thereafter the patient is imaged using planar gamma scintigraphy.

All of the foregoing are merely illustrative, and other equivalent embodiments are possible and contemplated.

Although the invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above, and of the corresponding application, are hereby incorporated by reference.

What is claimed is:

1. A high affinity chemotactic peptide-based pharmaceutical composition suitable for administration to a patient comprising:

a biological-function domain including at least two linked N-formyl-Met-Leu-Phe sequences wherein the sequences are linked by means of peptide side chains; and a medically useful metal ion-binding domain comprising a sequence of amino acids containing sulfur or nitrogen atoms which are available for metal ion binding.

2. The peptide-based pharmaceutical composition of claim 1 wherein said peptide comprising a biological-function domain and a medically useful metal ion-binding domain is selected from the group consisting of $(R_1)-[Y_1]_n-(R_2)$, $(R_1)-[Y_1-(R_2)-Y_1]_n-(R_3)$ and $(R_1)-[Y_1-(R_2)-Y_2]_n-(R_3)$ wherein, the medically useful metal ion-binding domain is selected from one of the group consisting of $[Y_1]_n$, $[Y_1-(R_2)-Y_1]_n$ and $[Y_1-(R_2)-Y_2]_n$ in which n is a number between 1 and about 6 and $Y_1$ and $Y_2$ are amino acids comprising a sulfur, nitrogen or oxygen which is available for binding to metal ions or can be made available for binding to metal ions;

the biological-function domain comprises at least one of the group consisting of $R_1$, $R_2$ and $R_3$; and those portions of $R_1$, $R_2$ and $R_3$ not comprising the biological-function domain each comprise an amino acid sequence containing from 0 to about 20 amino acids.

3. The peptide-based pharmaceutical composition of claim 2 wherein the medically useful metal ion-binding domain comprises at least one amino acid sequence consisting of at least one amino acid selected from the group consisting of cysteine, cystine, histidine, penicillamine, deacylated methionine, lysine, arginine, aspartic acid, glutamic acid and tyrosine.

4. The peptide-based pharmaceutical composition of claim 1 wherein said biological-function domain is a peptide sequence and linking agent comprising

```
N-formyl-Met—Leu—Phe—Phe—Lys—
                              |
                              linking agent
                              |
N-formyl-Met—Leu—Phe—Phe—Lys—.
```

5. The peptide-based pharmaceutical composition of claim 1 wherein said composition further comprises a metal ion labeling agent.

6. The peptide-based pharmaceutical composition of claim 5 wherein said metal ion labeling agent comprises a stannous ion agent.

7. The peptide-based pharmaceutical composition of claim 5 wherein said stannous ion agent comprises a member selected from the group consisting of stannous tartrate, stannous glucoheptonate, stannous gluconate, stannous phosphonate, stannous chloride, and stannous fluoride.

8. The peptide-based pharmaceutical composition of claim 5 wherein said composition further comprises a medically useful metal ion.

9. The peptide-based pharmaceutical composition of claim 8 wherein said medically useful metal ion comprises a member selected from the group consisting of the elements iron, cobalt, nickel, copper, zinc, arsenic, selenium, technetium, ruthenium, palladium, silver, cadmium, indium, antimony, rhenium, osmium, iridium, platinum, gold, mercury, thallium, lead, bismuth, polonium and astatine.

10. The peptide-based pharmaceutical composition of claim 8 wherein the medically useful metal ion is a radionuclide comprising an isotope selected from the group consisting of indium, gold, silver, mercury, technetium, rhenium and copper.

11. The peptide-based pharmaceutical composition of claim 8 wherein the medically useful metal ion is radioactive.

12. The peptide-based pharmaceutical composition of claim 1 wherein the composition is lyophilized.

13. A high-affinity chemotactic peptide-based pharmaceutical composition suitable for administration to a patient comprising:

a biological-function domain; and a medically useful metal ion-binding domain;

wherein said composition is selected from the group consisting of $(R_1)-[Y_1]_n-(R_2)$, $(R_1)$—$[Y_1$—$(R_2)$—$Y_1]_n$—$(R_3)$ and $(R_1)$—$[Y_1$—$(R_2)$—$Y_2]_n$—$(R_3)$ wherein the medically useful metal ion-binding domain is, respectively, $[Y_1]_n$, $[Y_1$—$(R_2)$—$Y_1]_n$ and $[Y_1$—$(R_2)$—$Y_2]_n$ in which n is a number between 1 and about 6 and $Y_1$ and $Y_2$ are amino acids comprising a sulfur, nitrogen or oxygen which is available for binding to a metal ion;

wherein the biological-function domain comprises at least one, or a portion of one, of the group consisting of amino acid sequences $R_1$, $R_2$ and $R_3$, which comprises at least two linked N-formyl-Met-Leu-Phe sequences;

wherein those portions of $R_1$, $R_2$ and $R_3$ not comprising the biological-function domain each comprise an amino acid sequence containing from 0 to about 20 amino acids;

wherein said medically useful metal ion-binding domain comprises at least one amino acid sequence consisting of at least one amino acid selected from the group consisting of cysteine, cystine, histidine, penicillamine, deacylated methionine, lysine, arginine, aspartic acid, glutamic acid, tyrosine, $[Cys]_n$, $[Cys$—$(R_2)$—$Cys]_n$, $[Cys$—$(R_2)$—$Pen]_n$, $[His$—$(R_2)$—$Cys]_n$, $[His$—$(R_2)$—$Pen]_n$, $[His]_n$ and $[His$—$(R_2)$—$His]_n$, wherein n is a number between 1 and about 6; and $R_2$ is independently an amino acid sequence containing from 1 to about 20 amino acids.

\* \* \* \* \*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: Peptide ( i i i ) HYPOTHETICAL: No ( i v ) ANTI-SENSE: No ( i x ) FEATURE:
        ( D ) OTHER INFORMATION: Xaa is N- formyl Met ( x i ) SEQUENCE DESCRIPTION: SEQ ID NO: 1:

Xaa Leu Phe Gly Gly His Gly Gly Cys
    1                  5

( 2 ) INFORMATION FOR SEQ ID NO:2:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: Peptide ( i i i ) HYPOTHETICAL: No ( i v ) ANTI-SENSE: No ( i x ) FEATURE:
        ( D ) OTHER INFORMATION: Xaa is N- formyl Met ( x i ) SEQUENCE DESCRIPTION: SEQ ID NO: 2:

Xaa Leu Phe Gly His Gly Gly His Gly His Gly Gly His
    1                 5                       10

( 2 ) INFORMATION FOR SEQ ID NO:3:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: Peptide ( i i i ) HYPOTHETICAL: No ( i v ) ANTI-SENSE: No ( i x ) FEATURE:
        ( D ) OTHER INFORMATION: Xaa is N- formyl Met ( x i ) SEQUENCE DESCRIPTION: SEQ ID NO: 3:

Xaa Leu Phe Gly Gly His Glu Lys Gly His Gly His Trp
    1                 5                       10

( 2 ) INFORMATION FOR SEQ ID NO:4:

( i ) SEQUENCE CHARACTERISTICS:

```
( A ) LENGTH: 7 amino acids
( B ) TYPE: amino acid
( C ) STRANDEDNESS: single
( D ) TOPOLOGY: linear ( i i ) MOLECULE TYPE: Peptide ( i i i ) HYPOTHETICAL: No ( i v ) ANTI-SENSE: No ( i x ) FEATURE:
      ( D ) OTHER INFORMATION: Xaa is N- formyl Met ( x i ) SEQUENCE DESCRIPTION: SEQ ID NO: 4:

Xaa  Leu  Phe  Gly  Gly  His  Trp
    1              5
```